(12) United States Patent
Virdee et al.

(10) Patent No.: US 8,099,295 B2
(45) Date of Patent: Jan. 17, 2012

(54) PRESCRIPTION CREATION AND ADJUDICATION METHOD

(75) Inventors: Pritpal S. Virdee, Ellisville, MO (US); Agnès Rey-Giraud, Chesterfield, MO (US); Elizabeth S. Wingate, Chesterfield, MO (US); Mike Stuart, Saint Charles, MO (US)

(73) Assignee: Express Scripts, Inc., St. Louis, MO (US)

( * ) Notice: Subject to any disclaimer, the term of this patent is extended or adjusted under 35 U.S.C. 154(b) by 1943 days.

(21) Appl. No.: 10/357,917

(22) Filed: Feb. 4, 2003

(65) Prior Publication Data
US 2004/0153336 A1 Aug. 5, 2004

(51) Int. Cl.
G06Q 10/00 (2006.01)
G06Q 50/00 (2006.01)
G06Q 40/00 (2006.01)

(52) U.S. Cl. ............................... 705/2; 705/4
(58) Field of Classification Search .................. 705/4, 2, 705/3
See application file for complete search history.

(56) References Cited

U.S. PATENT DOCUMENTS

| | | | | |
|---|---|---|---|---|
| 4,987,538 A * | 1/1991 | Johnson et al. | | 705/2 |
| 5,182,705 A * | 1/1993 | Barr et al. | | 705/11 |
| 5,324,077 A * | 6/1994 | Kessler et al. | | 283/54 |
| 5,550,734 A * | 8/1996 | Tarter et al. | | 705/2 |
| 5,704,044 A | 12/1997 | Tarter | | 395/204 |
| 5,737,539 A | 4/1998 | Edelson | | 395/203 |
| 5,845,255 A | 12/1998 | Mayaud | | 705/3 |
| 5,915,241 A | 6/1999 | Giannini | | 705/2 |
| 5,956,687 A * | 9/1999 | Wamsley et al. | | 705/1 |
| 6,014,631 A | 1/2000 | Teagarden | | 705/3 |
| 6,067,524 A | 5/2000 | Byerly | | 705/3 |
| 6,240,394 B1 | 5/2001 | Uecker | | 705/3 |
| 6,324,516 B1 * | 11/2001 | Shults et al. | | 705/2 |
| 6,915,265 B1 * | 7/2005 | Johnson | | 705/2 |
| 2001/0037216 A1 | 11/2001 | Oscar | | 705/2 |
| 2002/0002495 A1 * | 1/2002 | Ullman | | 705/21 |
| 2002/0007290 A1 * | 1/2002 | Gottlieb | | 705/4 |
| 2002/0032582 A1 | 3/2002 | Feeney, Jr. | | 705/2 |
| 2002/0035484 A1 | 3/2002 | Mccormick | | 705/2 |
| 2002/0035488 A1 * | 3/2002 | Aquila et al. | | 705/4 |
| 2002/0035528 A1 * | 3/2002 | Simpson et al. | | 705/35 |
| 2002/0042725 A1 | 4/2002 | Mayaud | | 705/2 |
| 2002/0042726 A1 | 4/2002 | Mayaud | | 705/2 |
| 2002/0049767 A1 | 4/2002 | Bennett | | 707/104.1 |
| 2002/0055856 A1 | 5/2002 | Adams | | 705/2 |
| 2002/0103680 A1 * | 8/2002 | Newman | | 705/4 |
| 2002/0128863 A1 * | 9/2002 | Richmond | | 705/2 |

(Continued)

OTHER PUBLICATIONS

National Council for Prescription Drug Programs, A Basic Guide to NCPDP Standards, Jan. 2002.

(Continued)

Primary Examiner — Neal Sereboff
(74) Attorney, Agent, or Firm — Bryan Cave LLP

(57) ABSTRACT

The invention provides a computer-implemented method for creating a prescription for treatment of an injury or illness covered by a workers' compensation system, which facilitates on-line adjudication of a workers' compensation claim. The patient name, employer name and type and quantity of medication prescribed are input. Routing data including a processor identification number is retrieved from an employer database. The program outputs prescription data comprising the name of the patient, the type and quantity of medication prescribed, and the routing data. The prescription data is preferably NCPDP compliant and used by a pharmacy to route a workers' compensation claim and fill the prescription.

10 Claims, 19 Drawing Sheets

U.S. PATENT DOCUMENTS

| | | | |
|---|---|---|---|
| 2002/0128883 A1* | 9/2002 | Harris | 705/4 |
| 2002/0138306 A1 | 9/2002 | Sabovich | 705/3 |
| 2002/0143582 A1* | 10/2002 | Neuman et al. | 705/3 |
| 2002/0173875 A1* | 11/2002 | Wallace et al. | 700/242 |
| 2003/0033169 A1* | 2/2003 | Dew | 705/3 |
| 2003/0093295 A1* | 5/2003 | Lilly et al. | 705/2 |
| 2003/0229522 A1* | 12/2003 | Thompson et al. | 705/4 |
| 2004/0054685 A1* | 3/2004 | Rahn et al. | 707/102 |

OTHER PUBLICATIONS

National Council for Prescription Drug Programs, Prescriber/Pharmacist Interface Script Standard Format, Jan. 2002.

National Council for Prescription Drug Programs, Telecommunication Standard, Jan. 2002.

National Council for Prescription Drug Programs, Telecommunication Standard Format, Feb. 11, 1992.

National Council for Prescription Drug Programs, Data Element Dictionary, Oct. 1998.

National Council for Prescription Drug Programs, Health Care Identification Card, May 2002.

National Council for Prescription Drug Programs, Prescriber/Pharmacist Interface Script Standard Format, Aug. 2001.

Express Scripts, Inc., archived Express Scripts Inc. web page describing a worker's compensation product line; retrieved from archive.org on May 6, 2011. According to archive.org, this web page was archived in 2001.

* cited by examiner

Patient Summary

Sample Patient
Age: 32 y    Gender: M

Change Patient    Patient Summary    Send Email
Rx Writer

Demographics — 1002
SSN:     999-88-7777
DOB:     4/1/1970
Phone:   (111) 222-3333
Email:   SPatient@isp.com
Address: 123 Main Street
         San Francisco, CA 94112

Employer Information — 1004
Name:    TechFirm
ID:      98765
Phone:   (510) 111-2222
Address: 123 Disk Drive
         San Francisco, CA 94112

Medications — 1006

| Medication | Dosage | Date | Filled | Actions |
|---|---|---|---|---|
| Naprosyn | 500 MG | 4/30/2002 | 4/30/2002 | Info |
| Roxicet | 5-500 MG | | | Info |

Insurance — 1008

| Insurance | Policy ID |
|---|---|
| ABC Insurance | 999987777 |

Workers' Compensation — 1010

| Injury Date | Claim ID | Actions |
|---|---|---|
| 4/6/2002 | 761230 | Write-Rx |

Pharmacies — 1012

| Pharmacy | Phone Number |
|---|---|
| Rite Aid #491 | |

Consent — 1014

| Consent Type | Expires | Comment | Actions |
|---|---|---|---|
| Full | 4/7/2003 | | Renew Refill |

View Pad
View Pad    Update

PRESCRIPTION CREATION AND ADJUDICATION METHOD

FIELD OF THE INVENTION

This invention relates to processing of data relating to prescription drugs and prescription drug benefits. More particularly, the invention provides a method for creating prescriptions that facilitate adjudication of claims for workers' compensation or prescription drug benefits.

BACKGROUND

Pharmaceuticals are usually sold through a third-party payment system in which pharmacies look directly to insurers or other obligors for primary payment. Pharmacies must rely on the payment practices and creditworthiness of third parties to collect for prescriptions provided to customers covered by a third-party payment plan.

The conventional prescription claims processing and payment system involves one or more entities providing one or more of a variety of functions. Generally, these parties include: the pharmacy, switch, processor and obligor.

A patient may make a claim under a health plan through the patient's pharmacy at the time the prescription is filled. Today most conventional pharmaceutical claims are adjudicated using an electronic on-line system. Pharmacy's generally submit claims in real-time to a claims adjudication network for processing.

A switch provides the means for relaying electronic claims data from the pharmacy to a processor. Based upon a Bank Identification Number ("BIN"), a unique number issued by the American National Standards Institute, which identifies the appropriate processor, the switch forwards messages from the service provider to the processor and returns the responses. In general, a switch does not provide or alter the content of any of the messages it routes, but is merely a communications conduit.

A processor is an entity that provides on-line claim adjudication services. A processor's responsibility is to adjudicate claims by applying the plan parameters (i.e., determining the acceptability of a claim based, for example, on a claimant's eligibility and coverage of the medication), and then to report the results to the plan sponsor on a scheduled basis. The processor may be, for example, a pharmacy benefit management company (PBM) or a company contracted to perform services on behalf of a PBM.

An obligor is an entity (e.g., a workers' compensation carrier, state fund, insurance company or employer) that is generally considered as ultimately responsible for making payment for the healthcare services.

The National Council for Prescription Drug Programs ("NCPDP") provides standard formats for third-party claims processing. For example, the NCPDP provides the following electronic message formats, which specify field number, field name, field type, field format, and field length positions: (i) transaction format for prescription, which includes fields such as BIN, version number, transaction code, processor code, pharmacy number, group number, cardholder identification number, date of fill, and prescription number; (ii) response format for eligibility verification or prescription claim, which includes fields such as BIN, transaction code, response status, and response data; and (iii) reversal format, which includes fields such as BIN, transaction code, processor code, pharmacy identification number, date of fill, and prescription number. Other NCPDP standard message formats include a workers' compensation claim format and Medicaid claim format, which are designed to accommodate the processing of drug claims covered by workers' compensation and Medicaid programs.

After a patient or customer presents a pharmacy with a prescription, the pharmacist utilizes an in-house computer prescription system and gathers the necessary information about the prescription, patient, and insurance. The pharmacist inputs this information into a personal computer. This information is then generally transmitted over the on-line network via switches which direct the outgoing messages to the appropriate processor.

In response to the pharmacy's claim, an NCPDP formatted adjudication message is then transmitted by the processor receiving the claim back through the same channels to the originating pharmacy. An adjudication is an evaluation of the validity of a claim by reference to the patient eligibility and the terms and conditions of the plan, such as drug products allowed, types of permitted drug interactions and dosages, and drug prices which will be reimbursed by the plan. The adjudication message normally contains adjudication/authorization information, the unique prescription number and the previously agreed upon price for that prescription. An adjudication message transmitted by a processor indicates the following three items of information about the claim: (i) that it has been received by the processor; (ii) that it has been reviewed by the processor against specifications established by the plan and agreed upon by the obligor; and (iii) that it has been indicated for disposition in one of three ways: approval, rejection or pending status.

Once a pharmacy receives a positive on-line adjudication response to a claim, it logs the claim as an approved claim receivable, dispenses the drug based on instructions from the doctor and awaits payment.

Persons covered by a health plan are typically issued an identification card by the health plan sponsor to facilitate reimbursement for covered healthcare services and prescription medications. The NCPDP has issued a standard format for prescription benefit card design. This format requires the inclusion of an "essential information window," where pharmacy personnel can quickly obtain information needed to submit the claim for on-line adjudication. The card includes a Bank Identification Number (RxBIN), a Processor Control Number (RxPCN), a Group Number (RxGrp) and a member identification number. The Bank Identification Number (BIN), also referred to as an International Identification Number (IIN), identifies the processor for network routing. Each processor has a unique BIN assigned by American National Standards Institute (ANSI). The Processor Control Number is a control number assigned by the processor for internal routing of the claim by the processor. The Group Number is also used by the processor for routing and processing the claim. It is often used to identify the cardholder group or employer group. The card often contains other information to facilitate fulfillment and reimbursement, such as co-payment information and contact information for the health plan sponsor.

When a patient receives a prescription that is covered by the health plan, the patient merely presents the prescription at a pharmacy, along with the patient's identification card. The card provides sufficient information to the pharmacy for the pharmacy to electronically adjudicate the claim at the pharmacy before filling the prescription. That is, the pharmacy can immediately confirm that the person and prescription are covered by the health plan and the amount of any co-payment due from the person. Thus, the electronic adjudication process provides the pharmacy assurance that the claim is covered and it will be paid.

In many instances, the plan sponsor pays the pharmacy at pre-negotiated reimbursement rates. Such negotiation can be done directly between the plan sponsor and the pharmacy or through a PBM. For example, a PBM may represent a number of obligors. The PBM negotiates discounts for pharmaceuticals and other terms with pharmacies on behalf of its clients.

Though the identification card system adequately facilitates the processing of prescription claims covered by health care plans, it does not facilitate the adjudication of prescriptions associated with workers' compensation claims. Medical treatment and prescriptions for work-related illnesses and injuries are not covered by most health plans. Typically, separate entities provide health plan and workers' compensation coverage to the employer. Workers' compensation coverage is typically provided at the employer level with blanket coverage for work-related illnesses and injuries suffered by any eligible employee. Workers' compensation claims are far less frequent than medical and drug benefit claims covered by most health plans. As such, the cost of keeping track of employees and issuing identification cards is not usually justified for the workers' compensation carrier given the average number of workers' compensation claims processed.

Pharmacies may be required by workers' compensation laws to fill prescriptions without charge to patients who present a prescription subject to a workers' compensation claim. However, pharmacies are unable to efficiently adjudicate prescriptions for workers' compensation claims because of a lack of coverage information. Since workers' compensation coverage is seldom provided by the same entity as regular health benefits coverage, pharmacies frequently do not know where to obtain reimbursement for workers' compensation medication claims and/or lack a convenient method for submitting such claims. The pharmacy may be able to obtain the name of the patient's employer, but it is usually impractical for the pharmacy to obtain the name of the workers' compensation carrier and to confirm that the claim is covered. Most pharmacies do not have staffing to call the employer and take other steps necessary to identify the obligor and submit the prescription bill for reimbursement.

Consequently, many pharmacies are forced to sell their workers' compensation prescription claims to third party billing companies. These companies pay the pharmacy a percentage of the dispensing price for the medication and then identify and obtain payment for the entire amount from the obligor, profiting from the difference. Because the obligor is not dealing directly with the pharmacy, the third party billing company can seek reimbursement at retail rates that are higher than the rates that a PBM may have negotiated with the pharmacy on behalf of the obligor.

These shortcomings of the current system of adjudicating workers' compensation prescription claims operate to the disadvantage of pharmacies, workers' compensation carriers, employers and consumers. Pharmacies loose revenues by being forced to sell workers' compensation claims to third party billing companies at a discount. Workers' compensation carriers are forced to pay for prescriptions at standard retail price, rather than at negotiated discount rates. Increased costs caused by the inefficiency of the current system are passed along to the employer, which is forced to pay higher insurance premiums to cover the increased costs. These costs are ultimately passed along to consumers who must pay higher prices for goods and services of the employer. Thus, there is a strong need for an improved method for adjudicating workers' compensation prescription claims.

The present invention overcomes the shortcomings of the conventional method described above, while providing a number of advantages to the physician, pharmacy, and workers' compensation carrier. For the physician, the present invention can reduce paperwork, facilitates eligibility confirmation, and reduce the administrative time spent on follow-up calls relating to such things as formulary, eligibility and Drug Utilization Review (DUR). For the pharmacy, the present invention can provide for quicker payment of bills, more revenue, less paperwork, reduced errors transcribing written prescriptions, and simplified administrative processing. For the workers' compensation carrier, the present invention can reduce prescription costs and allows quicker claim resolution and turnaround. The present invention provides these and other advantageous results.

SUMMARY OF THE INVENTION

The invention provides a computer-implemented method for creating a prescription, which facilitates on-line adjudication of a prescription drug claim. Input data identifying a patient and a type and quantity of medication prescribed is received. Routing data comprising data identifying a processor is retrieved from a database for associating the input data with routing data. Prescription data comprising an identification of the patient, the type and quantity of medication prescribed, and the routing data is output. The prescription data can be received by a pharmacy to route a claim to the processor for on-line adjudication and to fill the prescription.

In one embodiment, the method is used to create a prescription for treatment of an injury or illness covered by a workers' compensation system. The method facilitates on-line adjudication of a workers' compensation claim. Input data identifying a patient, an employer, and a type and quantity of medication prescribed are received. A patient database can be used to store and retrieve data relating to the patient. Routing data including data identifying the processor is retrieved from an employer database. The routing data can also include data identifying the workers' compensation carrier or employer. The program outputs prescription data comprising an identification of the patient, the type and quantity of medication prescribed, and the routing data. The prescription data is NCPDP compliant and can be received by a pharmacy to route a claim for on-line adjudication and to fill the prescription.

In one version of the method, the employer database includes coverage data that identifies a term of coverage associated with the workers' compensation carrier or employer. A date of injury is inputted by the user. Data associated with the worker's compensation carrier or employer is retrieved from the employer database and the program determines whether the date of injury falls within the term of coverage. A claim identifier (e.g., a claim number) associated with the injury can be generated and included in the prescription data. This claim identifier can be used to facilitate processing of later claims.

The prescription data can be output in a variety of ways. In one embodiment, a prescription including an identification of the patient and the type and quantity of medication is printed along with an identification card including the routing data. In another version the prescription itself includes an identification of the patient, the type and quantity of medication prescribed, and the routing data. Alternatively, the prescription data can be electronically transmitted to a pharmacy (e.g., via e-mail, fax or other means).

In another version of the method, the user can input data identifying a preferred pharmacy location. A pharmacy database including data identifying one or more pharmacies and associated locations is searched to identify one or more pharmacies near the preferred pharmacy location. The prescription data can include an identification of the retrieved pharmacies.

In another version, a drug database containing drug data relating to a plurality of drugs is provided. Drug data relating to one or more of the drugs is retrieved from the database and displayed on an input/output device such that the drug data can be selected and input by a user. The drug database can include SIG data comprising one or more common prescribing instructions. The SIG data can be retrieved from the database and displayed on an input/output device such that a common prescribing instruction can be selected and input by a user. The prescription data can include the selected common prescribing instruction.

The invention also includes a computer-implemented method for adjudicating a workers' compensation claim for a prescription for treatment of an injury or illness covered by a workers' compensation system. Data identifying a patient, an employer, and a type and quantity of medication prescribed are input by the user. Routing data is retrieved from an employer database for associating the data identifying the employer with routing data. The routing data includes data identifying a processor (e.g., an identification number). Prescription data including an identification of the patient, the type and quantity of medication prescribed, and the routing data is output. The prescription data is delivered to the pharmacy (e.g., by printing or electronic transmission). A claim for approval of reimbursement costs associated with the prescription is electronically routed by the pharmacy. It is determined whether the claim satisfies predetermined criteria for approval and a claim approval or disapproval message is electronically transmitted to the pharmacy.

DRAWINGS

These, and other features, aspects and advantages of the present invention will become more fully apparent from the following detailed description, appended claims, and accompanying drawings where:

FIGS. 3A and 3B are screens illustrating an embodiment of a patient search function of the method shown in FIGS. 1A-1E;

FIG. 4 is an example of a patient data entry screen for an embodiment of the method shown in FIGS. 1A-1E;

FIGS. 5A and 5B are screens illustrating an embodiment of an employer search function of the method shown in FIGS. 1A-1E;

FIGS. 7A and 7B are screens illustrating an embodiment of a medication selection function of the method shown in FIGS. 1A-1E;

FIG. 8 is an example of a medication data input screen of an embodiment of the method shown in FIGS. 1A-1E;

FIG. 10 is an example of a patient summary screen of an embodiment of the method shown in FIGS. 1A-1E; and FIG. 11 illustrates an embodiment of a prescription and identification card including routing data which facilitates on-line adjudication of a workers' compensation claim.

Figure 1A:
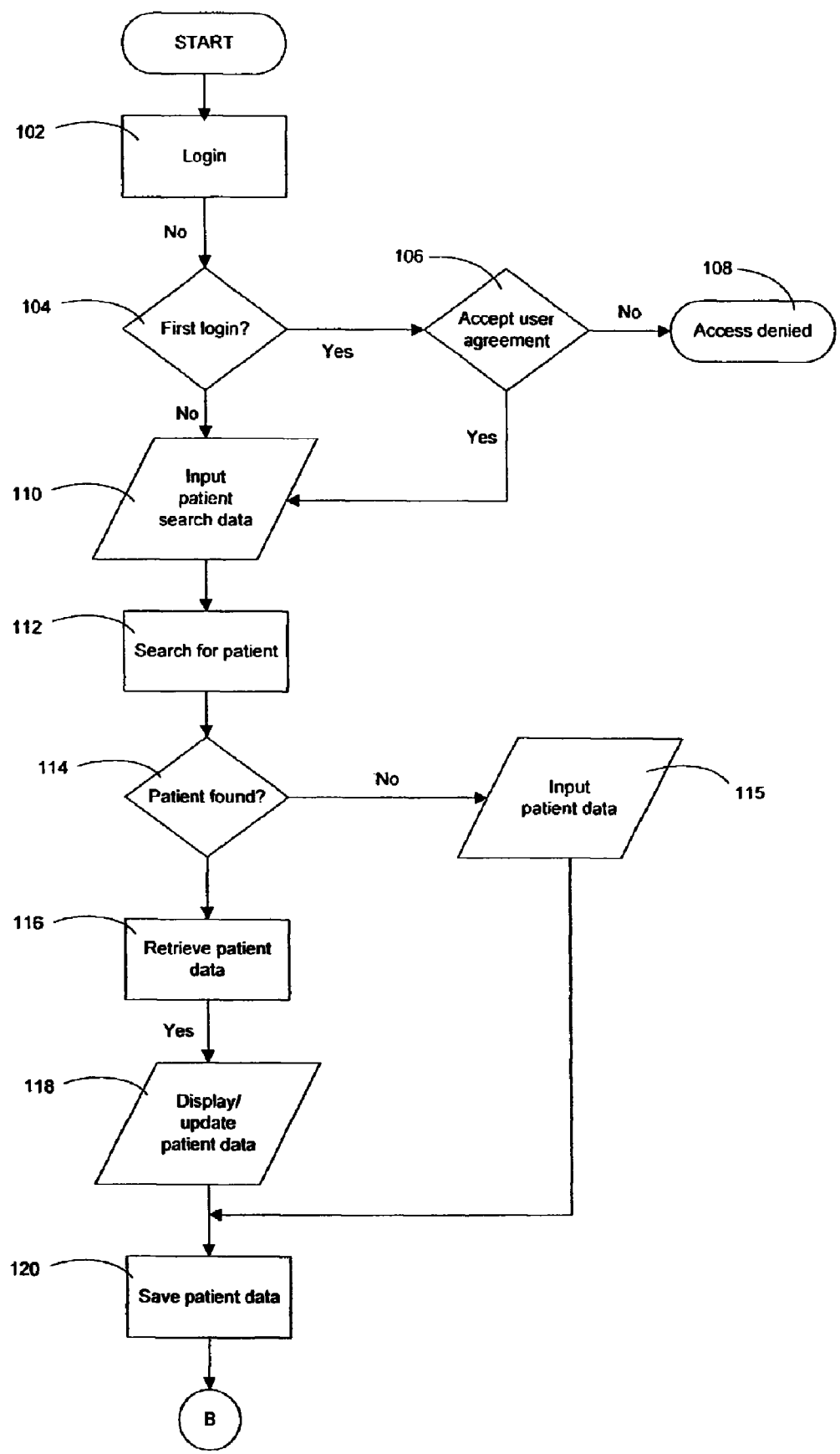
FIGS. 1A-1E are flow charts showing an embodiment of a computer-implemented method of creating a prescription which facilitates on-line adjudication of a workers' compensation claim.

For simplicity and clarity of illustration, the drawing figures illustrate the general steps of the method and features of the program. Description and details of well-known features and techniques are omitted to avoid unnecessarily obscuring the invention.

DETAILED DESCRIPTION OF THE PREFERRED EMBODIMENT OF THE INVENTION

The present invention is directed to a computer-implemented method for creating a prescription, which facilitates on-line adjudication of a prescription drug claim originated by the pharmacy filling the prescription.

"On-line adjudication" refers generally to the process by which a pharmacy electronically submits a claim for reimbursement for a prescription and receives approval or disapproval of the claim electronically. The claim is approved or disapproved by a "processor," which is any entity that provides on-line adjudication. For example, the processor can be a PBM that facilitates on-line adjudication of drug benefits on behalf of employers or insurance companies providing workers' compensation coverage.

As used herein, the term "prescription drug claim" refers generally to any claim for payment of costs associated with a prescription, including, for example, claims submitted for prescription drug benefits under a health plan or workers' compensation system. The preferred embodiment described in detail below with reference to FIGS. 1A-11 illustrates use of the method for a workers' compensation claim adjudication application. While the method is particularly adapted for use in facilitating adjudication of prescription drug claims covered by workers' compensation systems, the method can also be used to create prescriptions which facilitate on-line adjudication of other types of prescription drug benefits. For example, the method can be used to create prescriptions which facilitation processing of claims for drug benefits under health plans.

A preferred embodiment of the method is operated using software on a host computer supporting network delivery (e.g., via a secure Internet connection) to multiple remote users. The method can also be performed using various other system architectures, for example, using software on a standalone computer or on an office server accessible to a local area network of computers at a point of care. Personnel at the point of care are given access to the program through a computing device such as, for example, a desk-top or hand-held computer supporting a browser for communicating via a network such as the Internet with a host computer programmed to perform the steps of the method. As used herein, the term "point of care" refers broadly to any location at which medication is prescribed, such as, for example, a doctor's office, hospital, clinic, nursing home, treatment center or remote location. The user is preferably a physician or trained medical assistant.

Physician Registration/Login

The program preferably requires the use of a unique user name and password to provide system security and integrity. Each physician at the point of care is registered prior to login and assigned one or more user names and passwords. The data fields for registration include physician name, address, phone number, office contact, and Drug Enforcement Administration (DEA) number and/or medical license number and state.

The data captured during registration is stored in a database, which is preferably available in a report and/or extract format.

With reference to FIG. 1A, which generally illustrates a flow chart of a preferred embodiment of software embodying a method of creating a prescription which facilitates on-line adjudication of a workers' compensation claim, the program commences at step 102 where the operator logs into the system via a user interface at the point of care. At step 104, the program determines whether the login is the user's first. If it is, the user is preferably required to accept a user agreement at step 106. If the user refuses to accept the user agreement, access to the program is denied at step 108. If the user accepts, the user agreement, the initial login is completed and the program proceeds.

Figure 2:
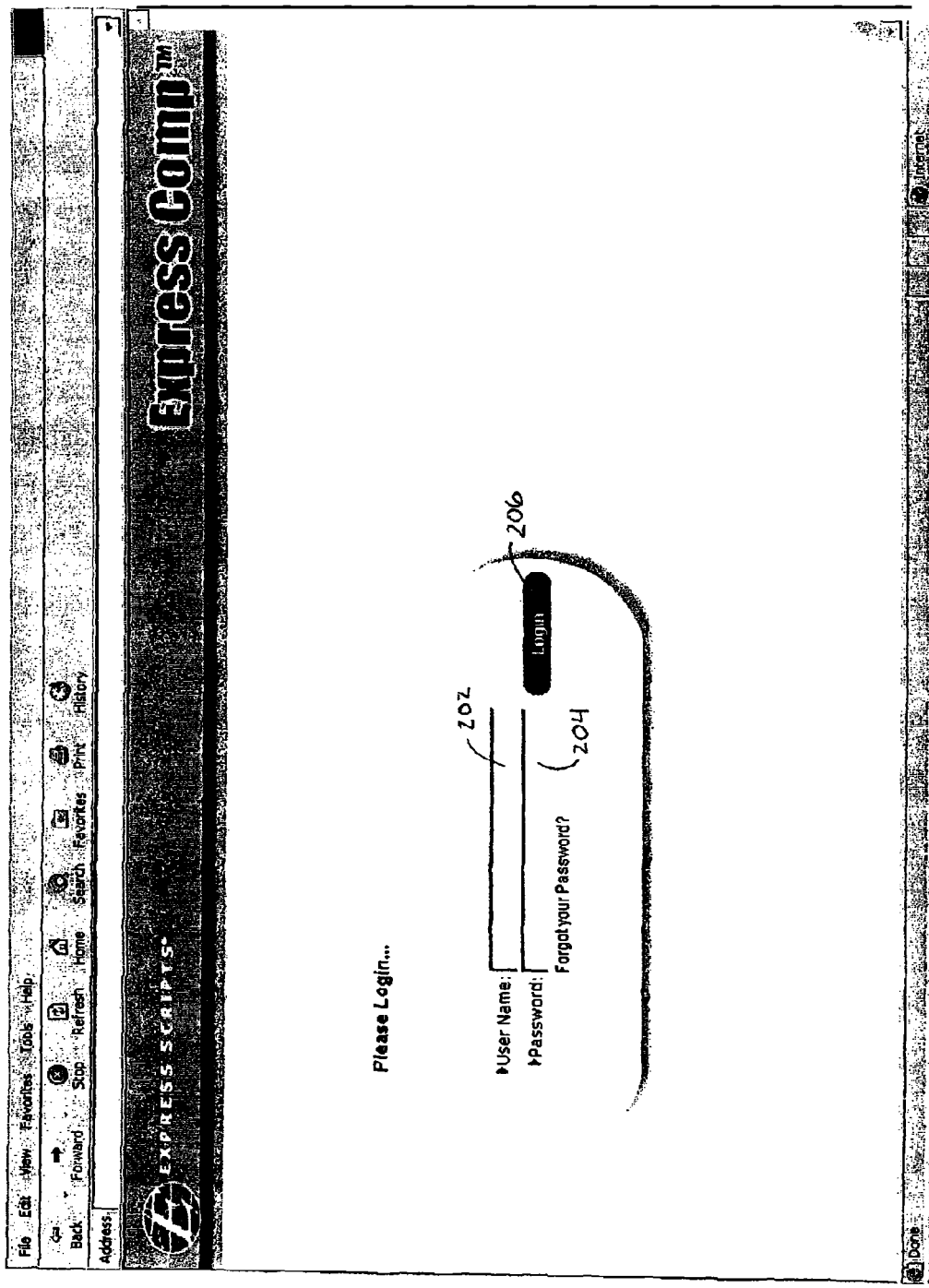
FIG. 2 is an example of a login screen for an embodiment of the method shown in FIGS. 1A-1E.

FIG. 2 illustrates an example of a login screen. The login screen can include a user name box 202 allowing an authorized user at the point of care to enter a unique user name that is associated with the physician. To provide additional security, the user is also preferably required to enter a unique password in password box 204 before accessing the program. The user can enter data using an input device such as, for example, a keyboard, mouse, touch screen, joystick, or microphone. The user can transmit the data by selecting login button 206.

Patient Data Entry

Referring again to FIG. 1A, after successfully logging into the system, the program prompts the user to input one or more fields of patient search data at step 110. The search criteria can include any patent identifying data that can be used to identify the patient or retrieve information relating to the patient from a database. Patient identifying data can include, for example, the patient's name, date of birth, social security number, phone number, or insurance or other identification number. As shown at step 112, the patient search data is used to search a database of previously entered patient data. The patient database preferably includes data for patients that have previously been given prescriptions using the system. The patient database can also include information otherwise previously entered (e.g., manually entered for each patient or transferred from another database).

At step 114, the program determines whether a patient has been found. If a patient is not found in the database, the program proceeds to a patient data entry screen as shown in step 115. If a patient is found and verified by the user, the program retrieves the previously entered patient data from the patient database as shown in step 116. At step 118, the information is displayed to the user via the user interface and the user so that can verify and/or update the information. Any changes or additions are preferably saved in the patient database at step 120.

Figure 3A:
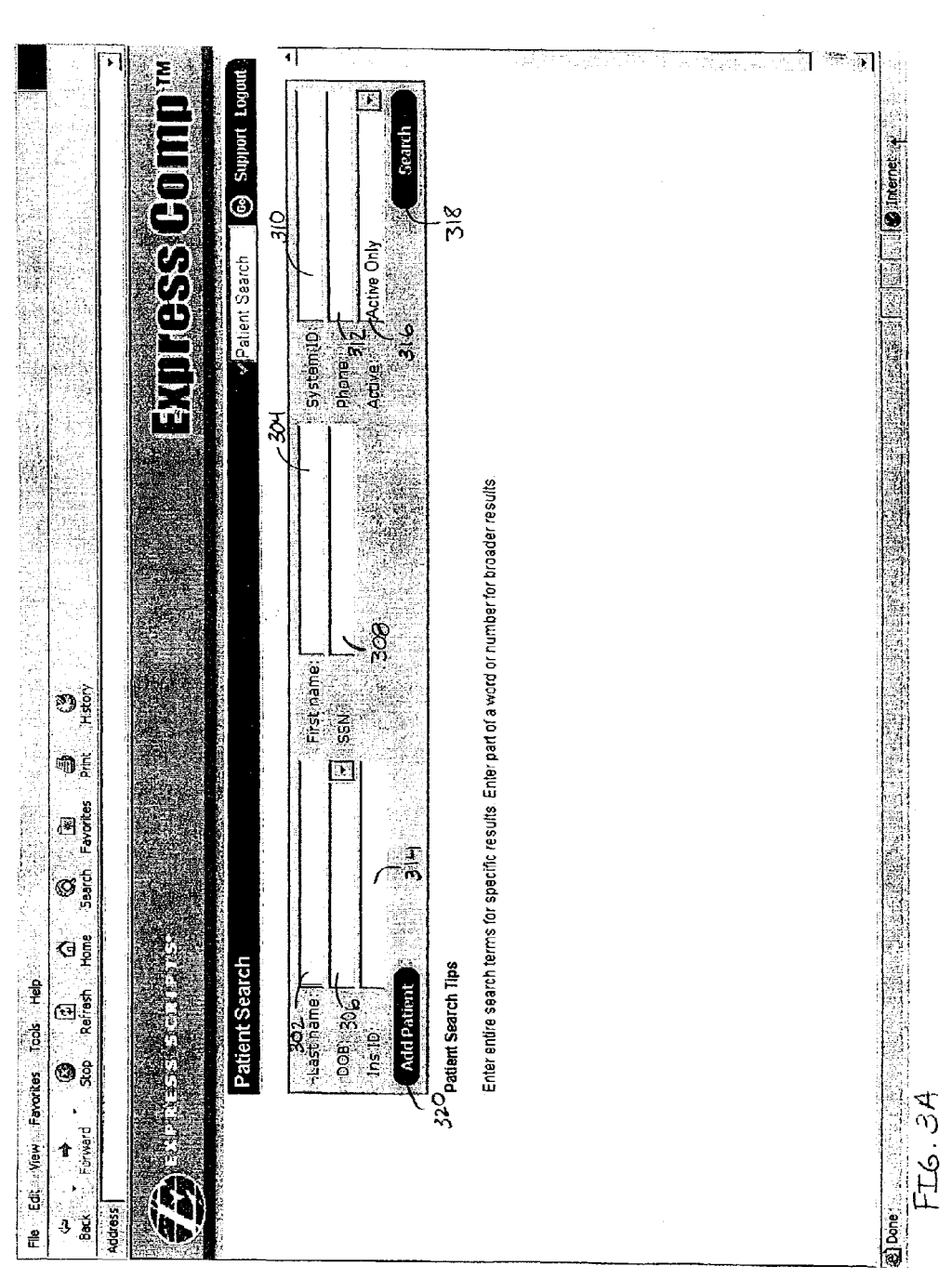

A patient search screen is illustrated in FIG. 3A. A database containing patient information previously entered into the system can be searched using one of various search fields. These fields are searched by entering text into one or more of various text boxes, which can include, for example, last name 302, first name 304, date of birth 306, social security number 308, system identification number 310, phone number 312, and insurance identification number 314. System identification box 310 can be used to enter an identification number assigned to the patient or patient's family in connection with a physician practice management system. By selecting the search button 318, the user transmits the entered search criteria. The host computer receives the search data input by the user and accesses a database of previously entered patient data to retrieve patient records matching the search criteria. Alternatively, the user can skip the search function and proceed directly to a patient data entry screen by selecting add patient button 320.

Figure 3B:
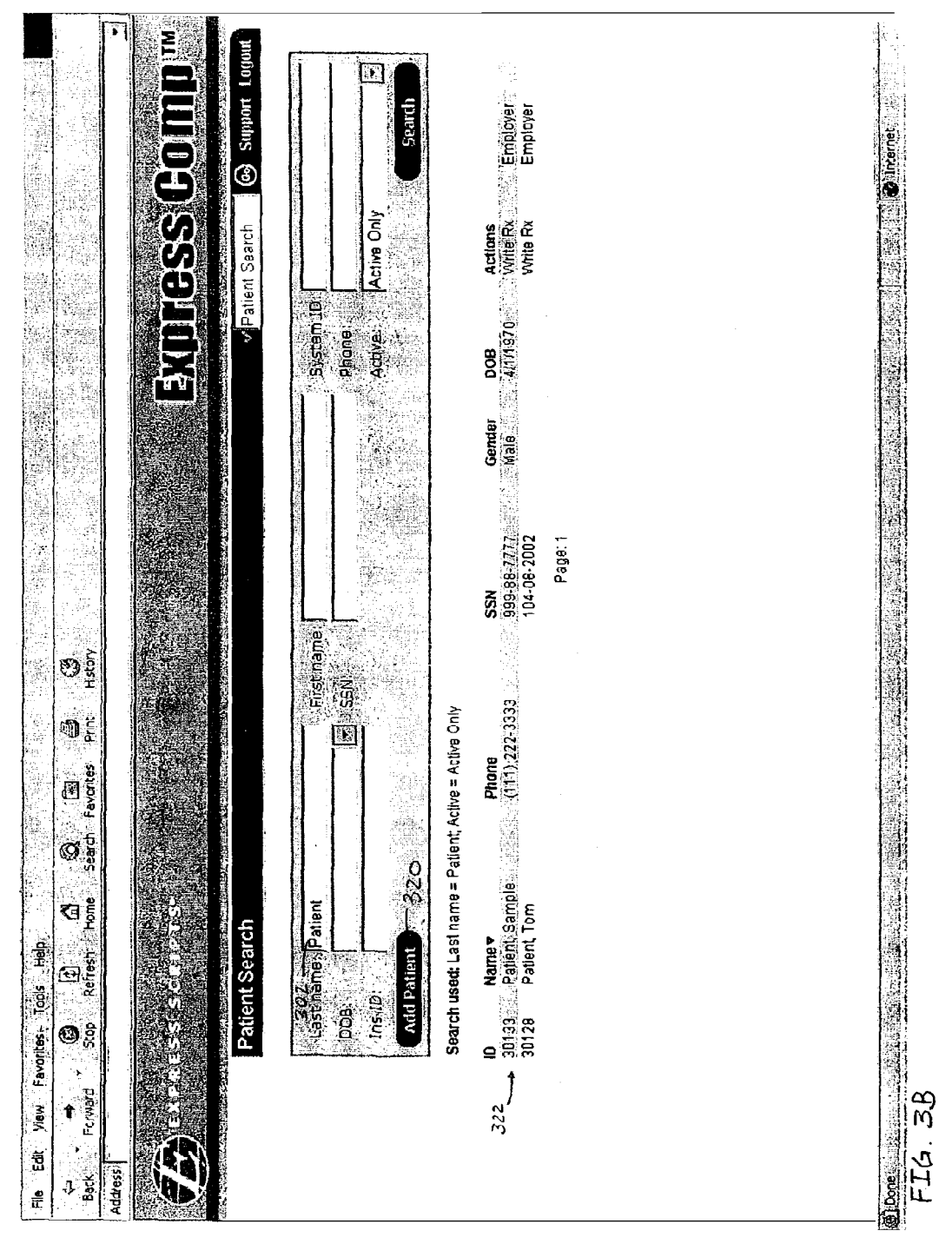

For example, with reference to FIG. 3B, the user can enter the patient's last name or a portion of the letters of the last name into last name text box 302. The program retrieves and displays a list of patients 322 having a last name corresponding to the letter string entered. The user can preferably select a patient record from the list. Alternatively, the user can perform one or more additional searches or add a new patient record by selecting the add patient button 320.

Figure 4:
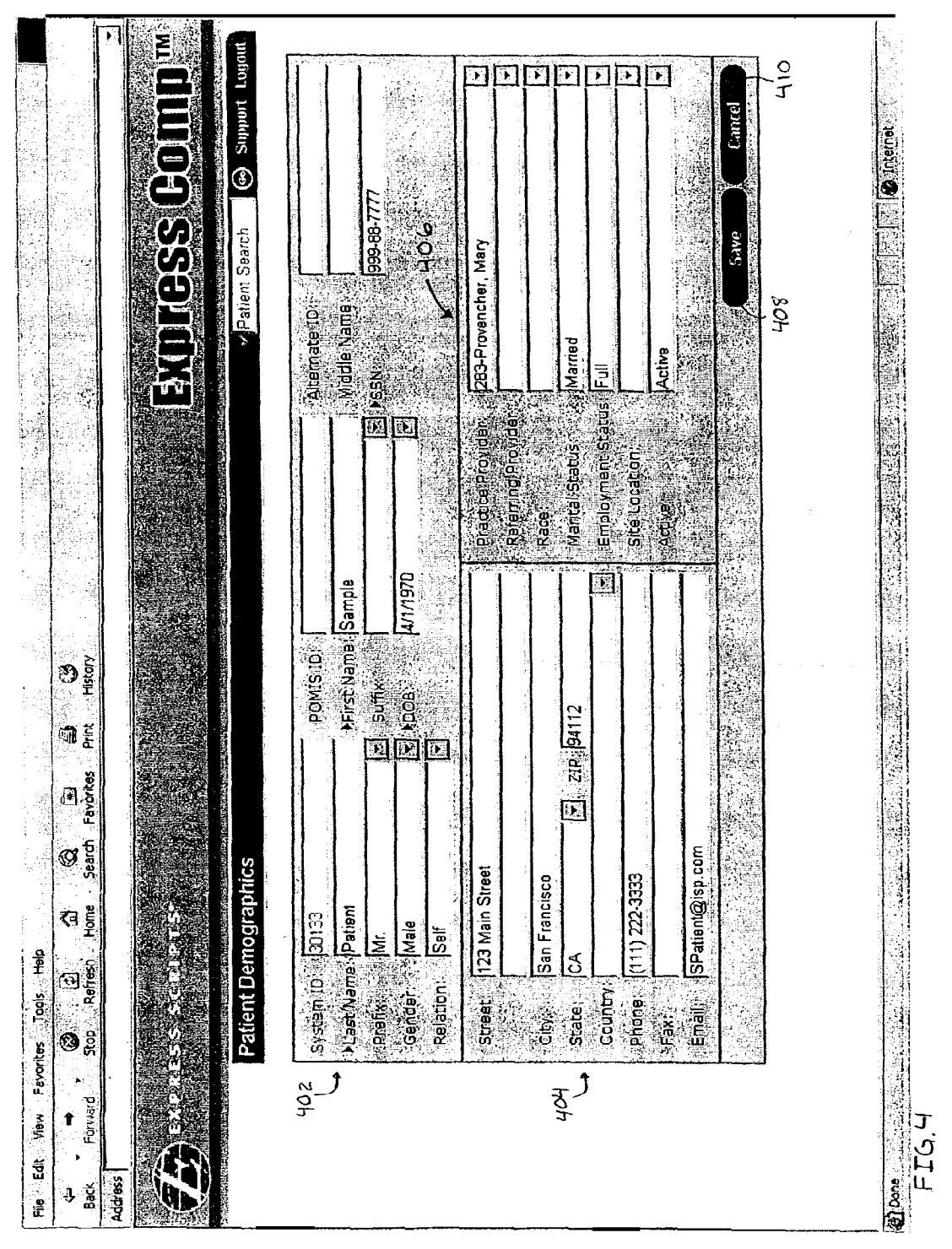

Selecting a patient record from list 322 or selecting the add patient button 320 prompts the program to display a patient data entry screen as shown in FIG. 4. In the example shown, the user has selected the first patient record in the list 322 (FIG. 3B). Data relating to that patient, which was previously entered into the patient database, is displayed. The patient data entries can include various data associated with the patient, for example, patient identifying data 402 (e.g., name, social security number, other identification numbers and the like), address and contact information 404, and various other data fields 406 (e.g., provider information, race information, marital status, employment status, site location, and whether the patient record is active). At this screen, the user can change data or enter new data if desired. If the user previously selected the add patient button 320, the data boxes displayed on the patient data entry screen will all be blank and the user can enter data into the various data boxes. Data entered by the user may be saved by selecting save button 408 or canceled by selecting cancel button 410. If the user selects the cancel button 410, the changes are canceled and the user returns to the search screen (FIG. 3A). If the user selects the save button 408, the a patient employer screen is displayed.

Employer Data Entry

Figure 1B:
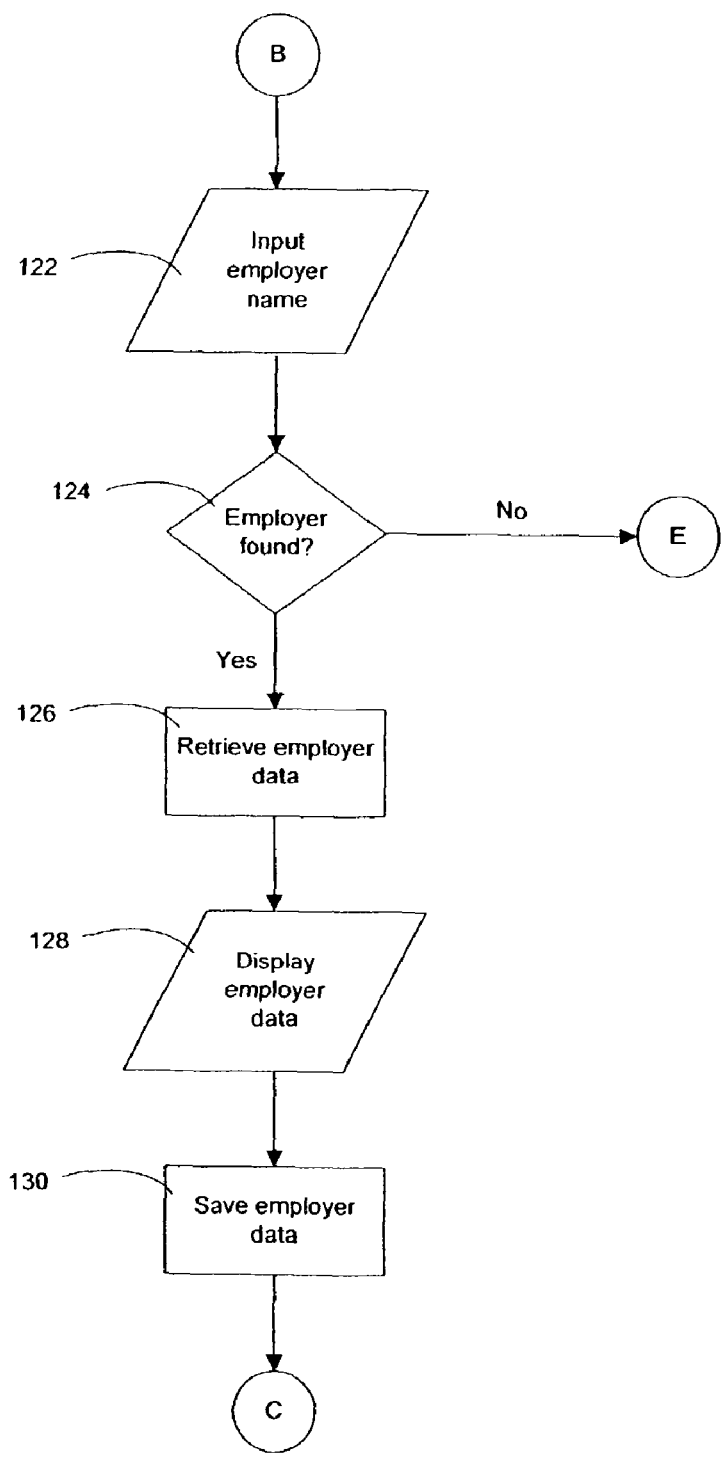

Referring now to FIG. 1B, once the patient data has been entered, the program conducts a search of an employer database to determine if the patient's employer at the time of injury is an eligible employer (i.e., participating in the on-line adjudication system). At step 122, the name of the patient's employer at the time of injury or other employer identifying data (e.g., an identification number) is input by the user. The employer identifying data can be any data that identifies or is associated with the employer, or can be used to identify the employer (e.g., by referencing a database). At step 124, the program determines whether the employer is contained in the database of eligible employers. If the employer is found within the employer database, employer data is retrieved from the database at step 126. This data includes information regarding the workers' compensation carrier of the employer and routing data. As used herein, the term "workers' compensation carrier" generally refers to any entity (e.g., insurance company or employer) ultimately responsible for payment of the workers' compensation claim. "Routing data" refers broadly to any data that facilitates electronic adjudication of a prescription claim. The employer data is displayed to the user at step 128. The employer data is saved in the patient database at step 130.

Figure 5A:
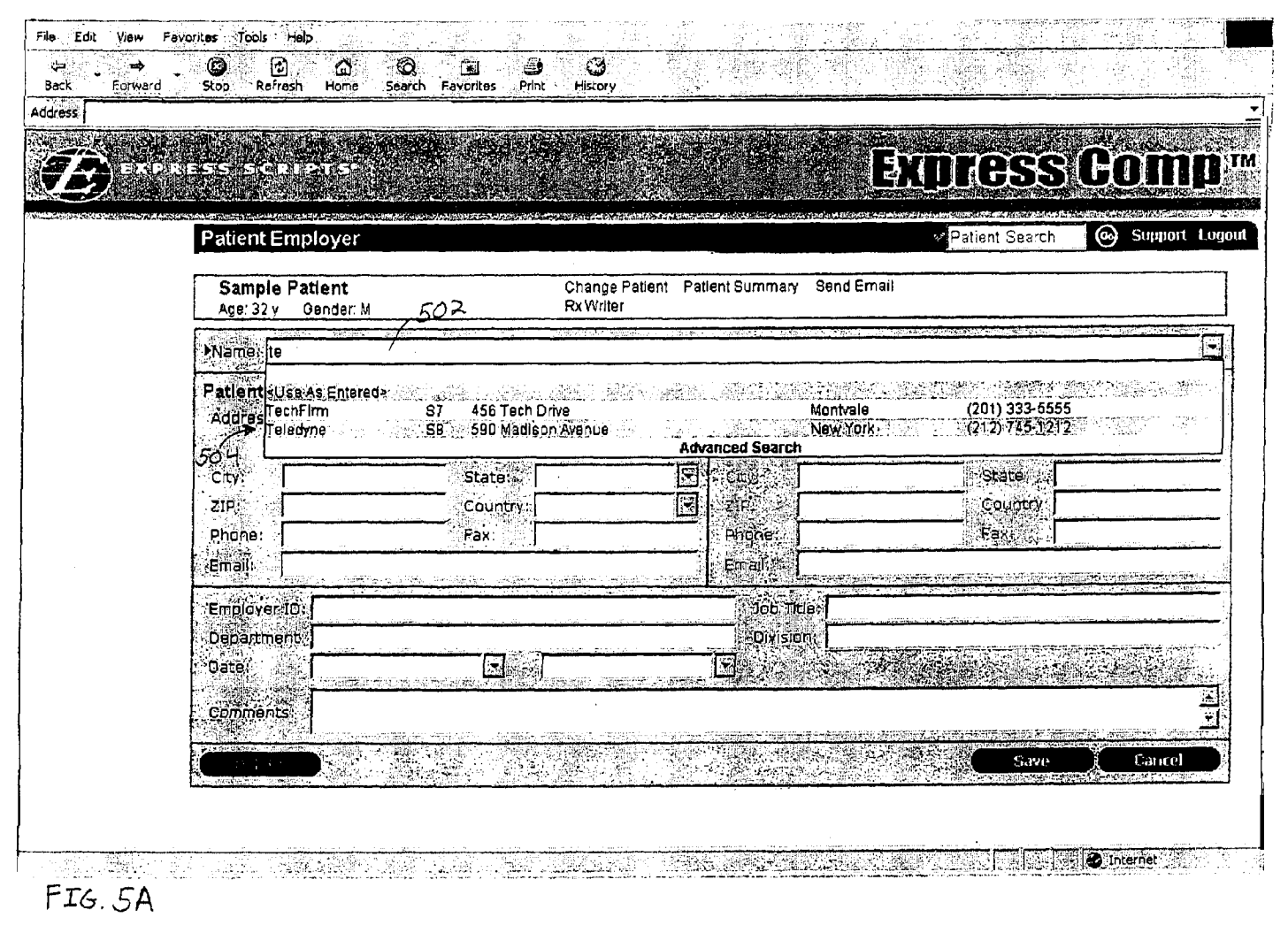

FIG. 5A illustrates an employer data entry screen. The screen preferably includes an employer name text box 502. The user can enter the employer's name (as indicated by the patient) or a text string comprising a portion of the name in the text box 502. The entry of data into text box 502 prompts the program to search an employer database. The employer database includes a list of employers covered by workers' compensation carriers participating in the system. The employer database also preferably includes any alternative names of the employer, the effective date of the workers' compensation coverage, the term of the coverage, and an identification of the workers' compensation carrier. Table 1 below shows an example of data that can be included in each employer record of an employer database.

TABLE 1

Employer Database

Employer Record
    Employer Carrier Code
    Employer Name
    Employer Address
    Employer City
    Employer State
    Employer Zip
    Employer Effective Date
    Employer Term Date
    Employer Policy Number
    Employer Carrier Name In the example shown in FIG. 5A, the entry of the data string "te" prompts the host computer to retrieve from the employer database a list of employers whose names begin with the letters "te." In the example shown, the user can select one of the employers from a list of employers displayed in a drop down menu 504.

Figure 5B:
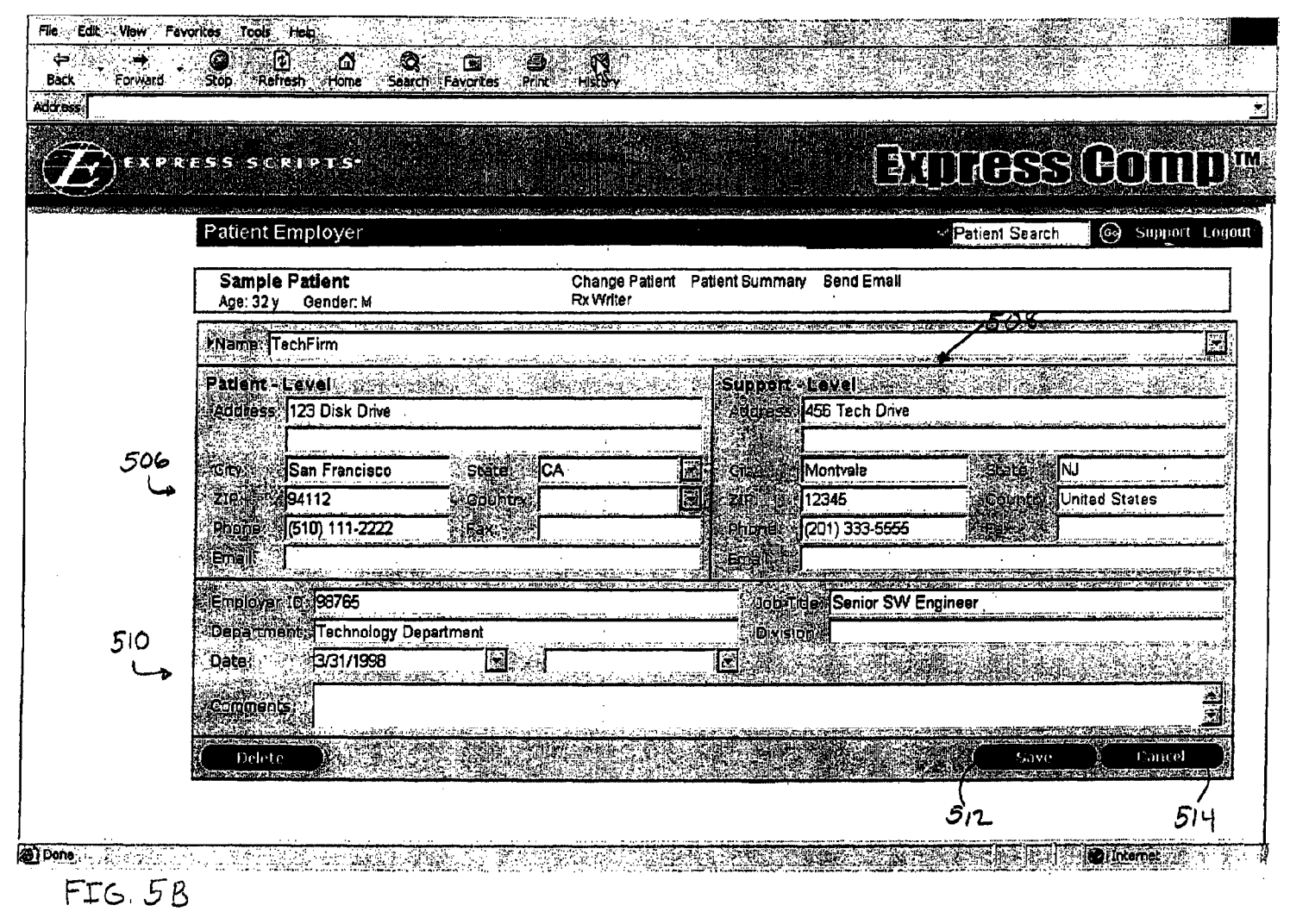

If a participating employer is identified in the employer database and selected by the user, data relating to that employer is retrieved from the database and displayed on the patient employer screen. Referring now to FIG. 5B, the information displayed can include patient-level information 506, including the mailing address, telephone number and e-mail address of the employer. The employer information may also include support level information 508, which can include the mailing address, telephone number, and e-mail address of the employer's support staff (e.g., the employer's benefits department). The employer information may also include other information 510 relating to the employer (e.g., an employer identification number) or employee (e.g., job title, department and date of employment). The user can preferably enter or modify selected fields of the employer information displayed. Data entered by the user may be saved in a record associated with the patient in the patient database by selecting save button 512 or canceled by selecting cancel button 514. The user may also select a delete button 516 to delete data relating to the selected employer from the patient's record. If the user selects the save button 512, the a workers' compensation case screen (FIG. 6A) is displayed.

Worker's Compensation Case Data Entry

Figure 1C:
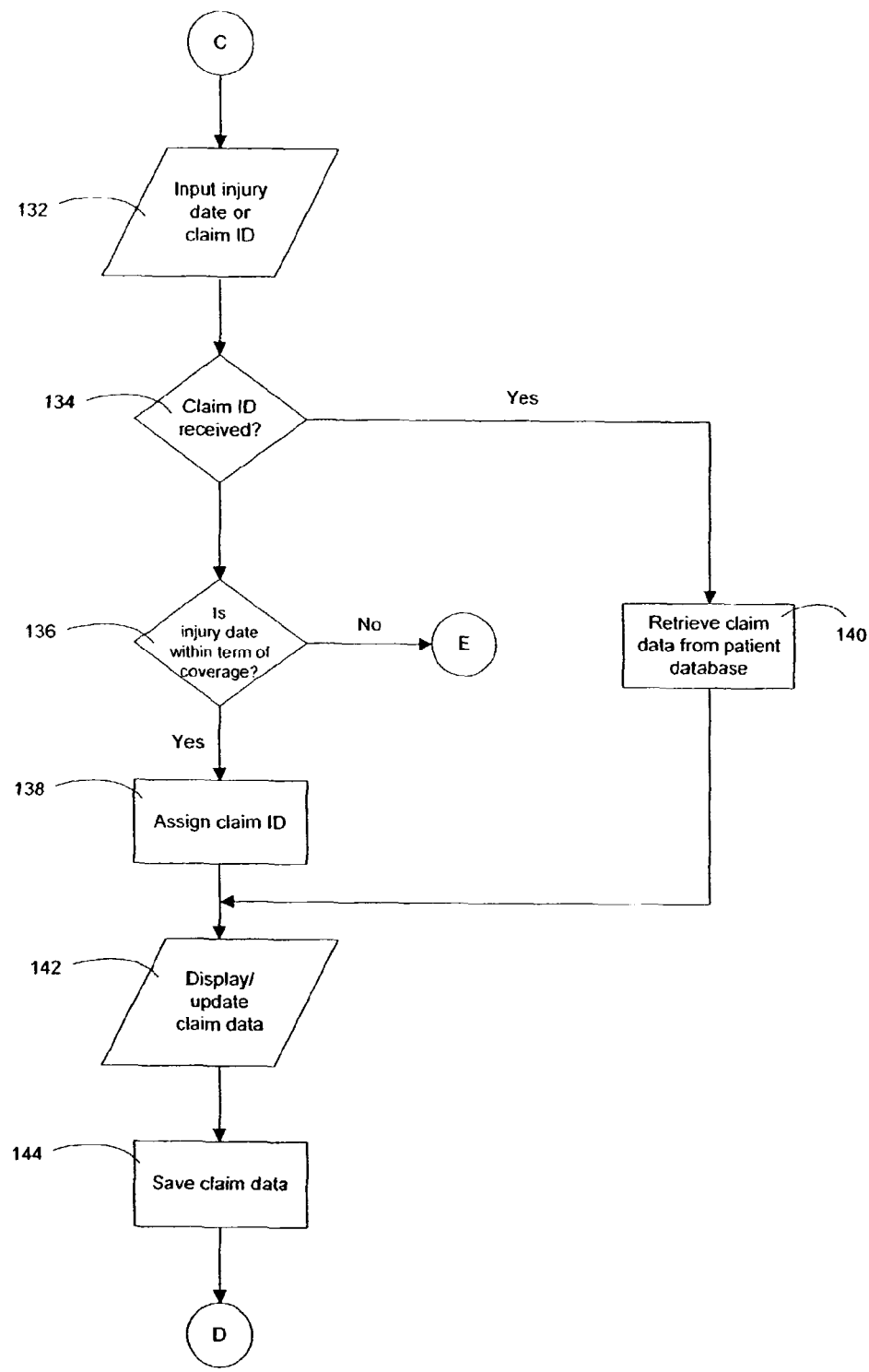

Referring now to FIG. 1C, once the user has saved information relating to the patient's employer, the user is prompted to input information relating to the injury. At step 132, the user inputs either a previously assigned claim identification number or the date of the injury associated with the prescription. The employer database preferably includes workers' compensation claim coverage data, which is any data that can be used to determine whether the claim falls within the scope of coverage. For example, the coverage data can include a term of coverage associated with the employer. The term of coverage provides the effective date and termination date of the workers' compensation insurance policy associated with a workers' compensation carrier. As illustrated at step 134, if an injury date is selected, the program searches the employer database to verify that the injury date falls within the term of the workers' compensation policy coverage as shown at step 136. If the injury date falls within the term of coverage, a claim identification number is assigned at step 138. Alternatively, if the patient has previously received treatment for the injury and a claim identification number has been issued, the user can input the claim identification number associated with an injury. The claim identification number is a number associated with a particular worker's compensation claim. Claim data is retrieved from the patient database at step 140. At step 142, claim data is displayed to the user. The user can preferably modify the claim data. After completing review, claim data associated with the claim number is saved to the patient database as illustrated at step 144.

Figure 6A:
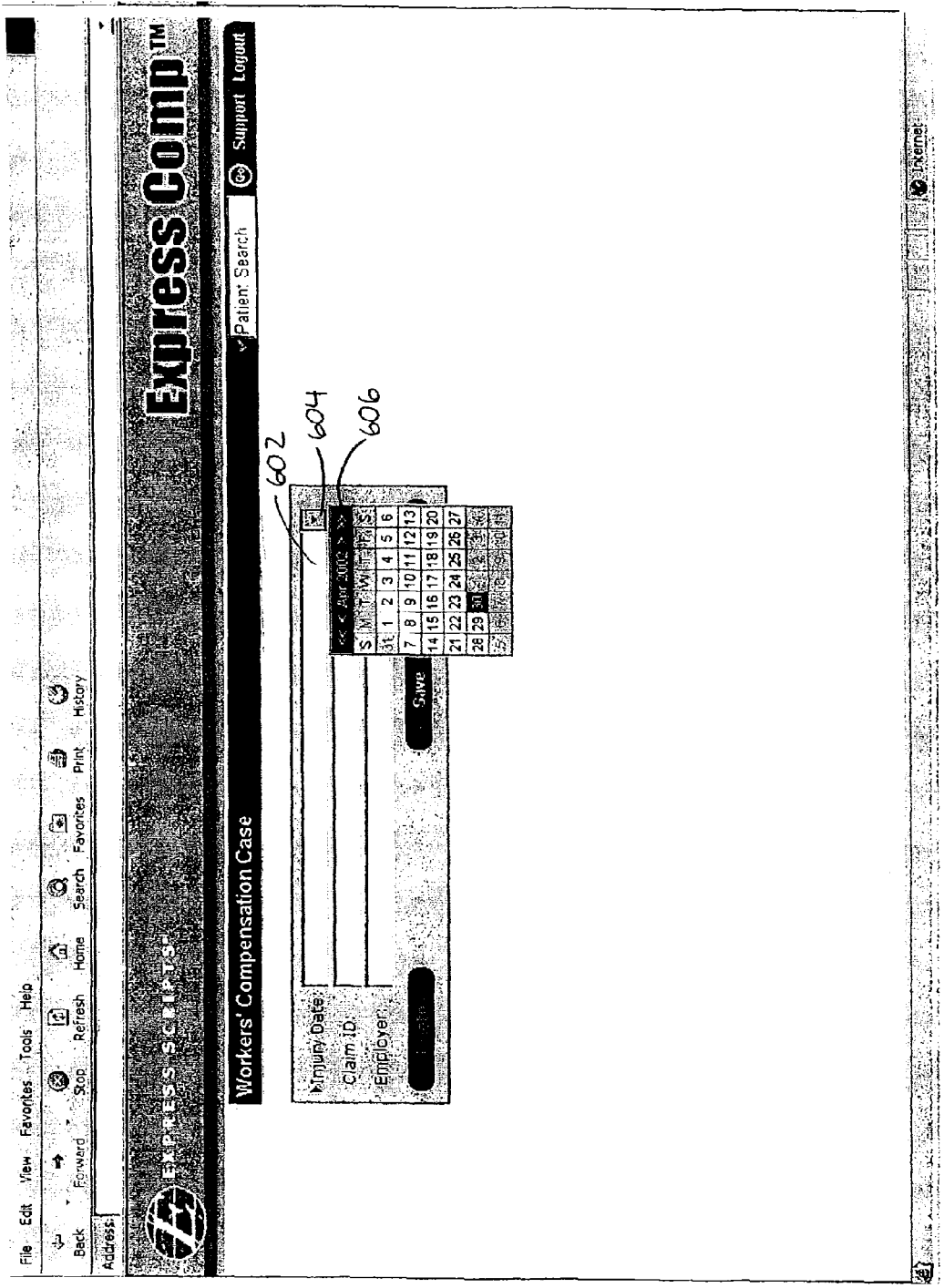
FIGS. 6A and 6B are screens illustrating an embodiment of an injury data input function of the method shown in FIGS. 1A-1E.
Figure 6B:
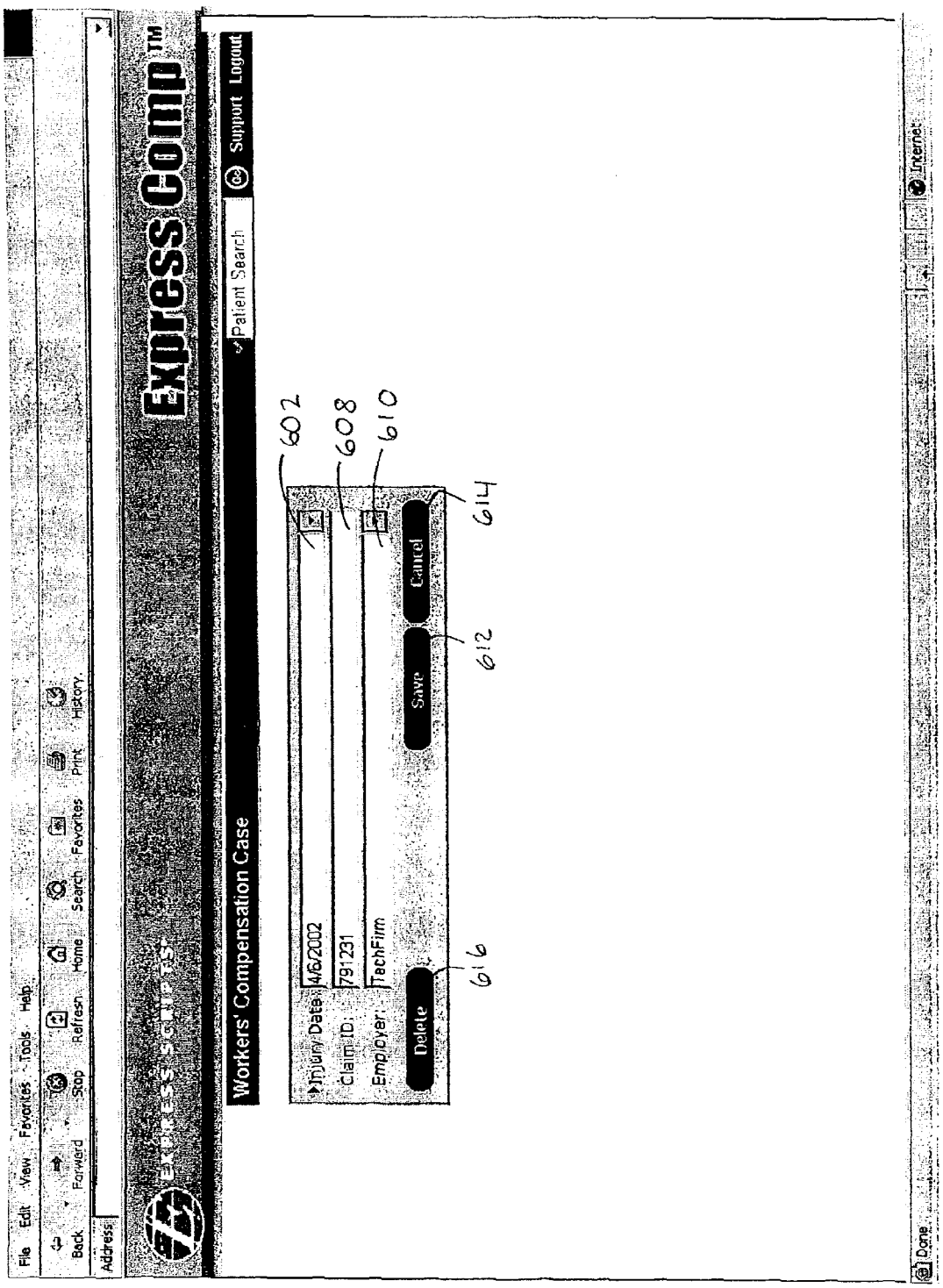

FIGS. 6A and 6B illustrate an example of a workers' compensation case screen for capturing information relating to the injury. The user can enter an injury date into an injury date text box 602. The text box 602 preferably includes a pull down menu 604 providing a calendar 606 for conveniently selecting an injury date.

If the injury date falls after the employee's date of employment and within the term of the workers' compensation policy coverage, a claim identifier (e.g., a claim identification number) will appear in text box 608. As used herein, the term "claim identifier" refers to any designation (numbers, letters, codes or the like) used to identify claims associated with a particular illness or injury. Only one claim identifier is associated with an injury date. The name of the employer at the time of the injury will appear in text box 610. The user may change data displayed on the workers' compensation case screen. Changes entered by the user may be saved by selecting save button 612 or canceled by selecting cancel button 614. The user may also select a delete button 616 to delete data relating to the workers' compensation case from the patient's record.

Prescription Writing

Figure 1D:
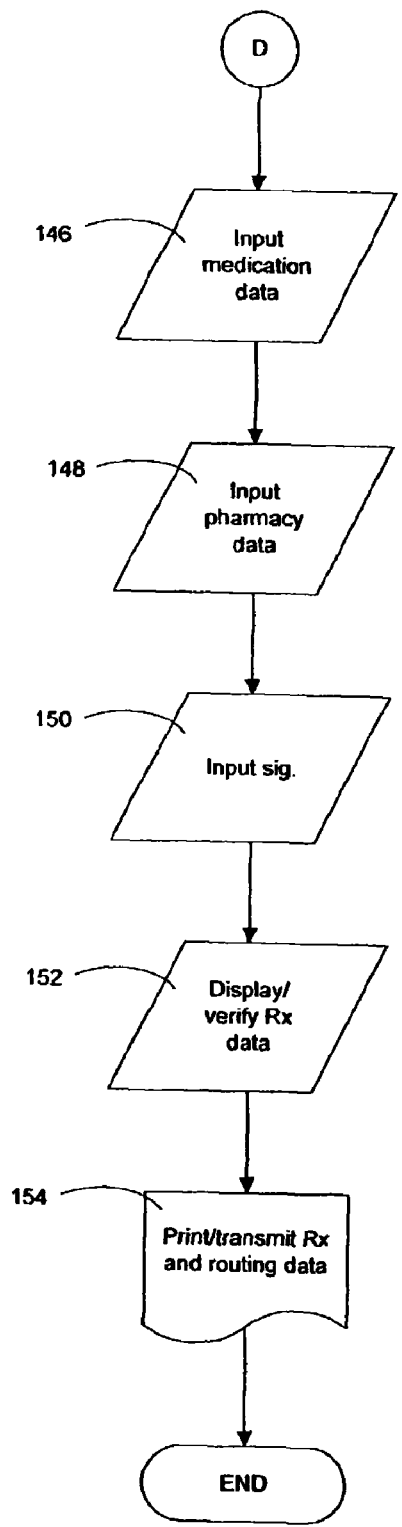
Figure 1E:
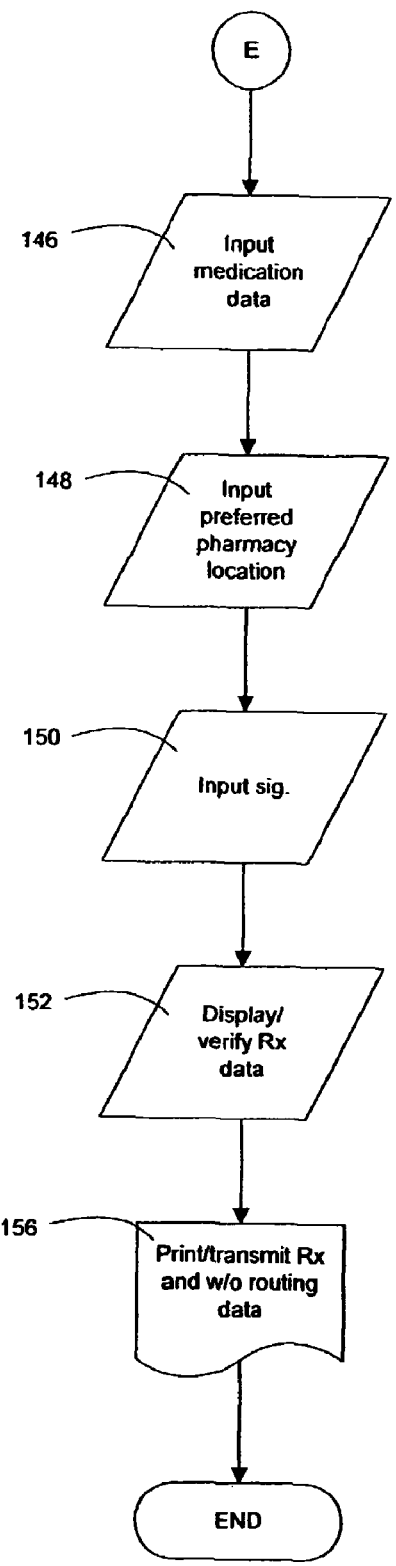

With reference to FIGS. 1D and 1E, the prescription writing function can preferably be performed whether or not the employee's worker's compensation claim is attributable to an eligible employer participating in the system. FIG. 1D illustrates an example of the writing function for and eligible employer and FIG. 1E illustrates the writing function for a non-eligible employer.

In either case, at step 146, the user inputs medication data including the type and quantity of medication prescribed. This step may include selecting the prescribed medication and quantity from a list retrieved from a drug database as described below with reference to FIGS. 7A and 7B.

At step 148, the user inputs pharmacy data. This data identifies the name and location of the pharmacy at which the patient would like to go to fill the prescription. At this step, the user may perform a search of network pharmacies as discussed below with reference to FIG. 7A. The program preferably encourages the user to select a network pharmacy so that the PBM or other entity facilitating the program can negotiate favorable prescription prices with the network pharmacies on behalf of participating worker's compensation carriers. Thus, it can be seen that one of the many advantages of the present invention is that it allows the workers' compensation carrier to pay negotiated prescription reimbursement rates. Such negotiation has generally not been feasible in the past using conventional worker's compensation reimbursement methods because pharmacies did not deal directly with workers' compensation carriers, but submitted claims through third-party billing agencies.

At step 150, the user inputs the Sig. As used herein, the term "Sig." refers to instructions or other information printed on the medication label. At this step, the user may select from a menu of common Sigs. for the prescribed medication contained in a drug database, as discussed below with reference to FIG. 8.

Once the medication data, preferred pharmacy location data, and Sig. have been entered, the program displays the prescription data to the user at step 152 so that the user can verify the data. As used herein, the term "prescription data" refers generally to data used to create a prescription embodied either in printed or electronic media. Once the prescription data has been verified, the user can print the prescription data or transmit it electronically to the selected pharmacy.

If the employer is an eligible employer, the printed or transmitted prescription data includes routing data as illustrated at step 154 of FIG. 1D. As discussed in greater detail below, the routing data allows the pharmacy filling the prescription to route a reimbursement claim for on-line adjudication. If the prescription is being written for a non-eligible employee, as illustrated in FIG. 1E, the printed or transmitted prescription does not include routing data as shown in step 156.

Figure 7A:
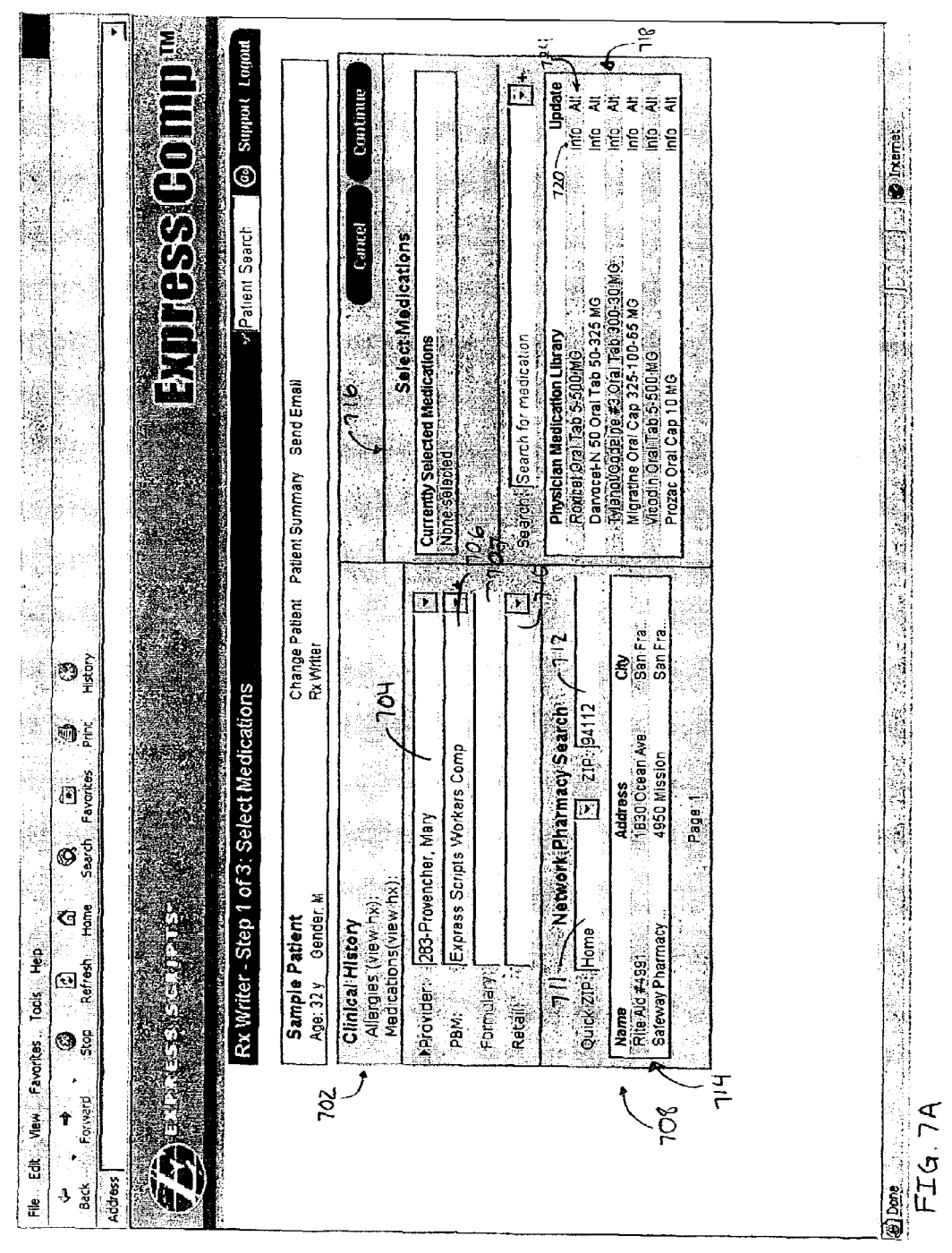
Figure 7B:
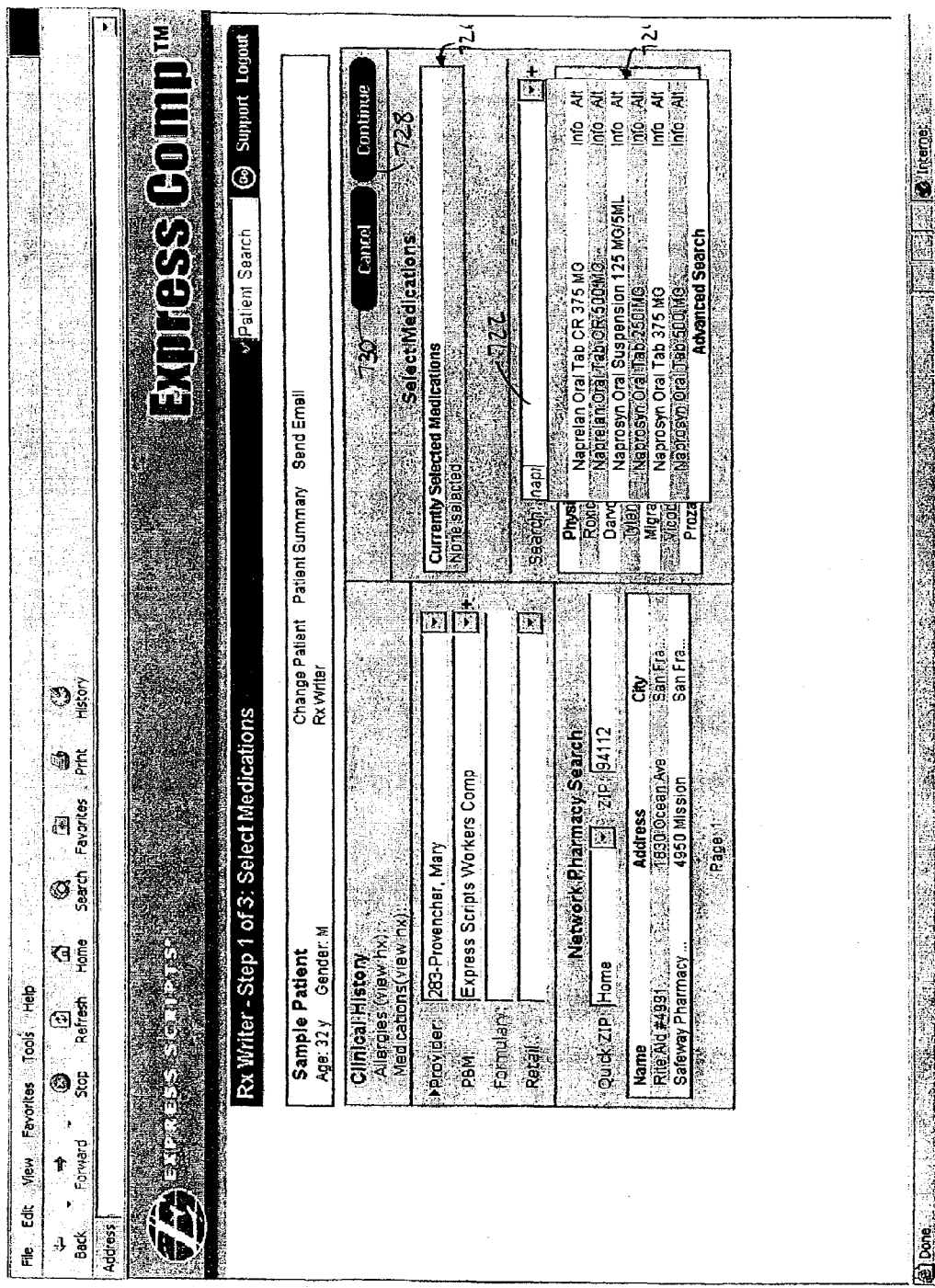

FIGS. 7A and 7B illustrate an example of an initial screen of a prescription wiring function. Clinical history information 702 is displayed to the user. Such information can include, for example, known allergies and medications to which the patient is allergic. Provider text box 704 allows the user to enter provider information. Preferably, the user can select from a list of providers associated with the user or point-of-care by using a drop down menu. PBM text box 706 can be used to allow the user to select a pharmacy benefits manager associated with the patient, preferably using a drop down menu. The formulary text box 707 can be used to provide an indication as to whether the prescribed medication is included in the patient's formulary by comparing the prescribed medication to a list of medications contained in a formulary database.

The retail text box 710 can be used to select a pharmacy from a list of pharmacies using a drop down menu. The patient can also select from a list of network pharmacies using a network pharmacy search function 708. The user can conduct a search using the zip code pull down menu 712. The user can preferably select "home," "office" or "physician's office" to identify a list of network pharmacies within or near the patient's home zip code, office zip code or the zip code of the physician's office. By selecting one of these options, the program will be prompted to retrieve the patient's home or office or the physician's office's zip code from a database and conduct a search of a network pharmacy database for pharmacies within or near the selected zip code. Alternatively, the user can conduct a pharmacy search by entering a zip code into the zip code text box 712. The system will be prompted to search for a network pharmacy within or near the zip code entered. Once the search is complete, a list of pharmacies 714 is displayed to the user. The user can consult with the patient and select one of the listed pharmacies.

The user selects medications using the select medications function 716. The user can search for drugs contained in a drug database. Updated drug databases along with common prescription amounts and information relating to each drug can be licensed from pharmaceutical data providers such as First Databank. A list of the most frequently prescribed drugs 718 is displayed to the user. Physicians, particularly specialists, often repetitively prescribe the same group of drugs. The frequently prescribed drug list 718 allows the user to conveniently select a medication from a list of medications frequently prescribed by the physician or at the point of care. This list can be created by or for the physician or point of care and stored in a database. Alternatively, this list can be created by recording in a database drugs actually prescribed by the user. This list can also be patient specific, listing the last group of drugs prescribed to the particular patient. The user can obtain further information on the drugs contained in the drug database by selecting information link 720 or can identify alternative medications by selecting alternative medication link 724.

As shown in FIG. 7B, the user can also search for drugs by entering the drug name or a text string comprising a portion of the name of the drug into text box 722. In the example shown, the user has entered the text string "napr" to retrieve a list of drugs beginning with the letters "napr." The user uses a drop down menu 724 to scroll through and select a drug from the list of drugs containing the entered letter string. The selected drugs will appear in a currently selected medications list 726. The user can preferably delete or change any entry. The user can continue to the next step of the prescription writing process by selecting the continue button 728 or can cancel the prescription by selecting the cancel button 730.

Figure 8:
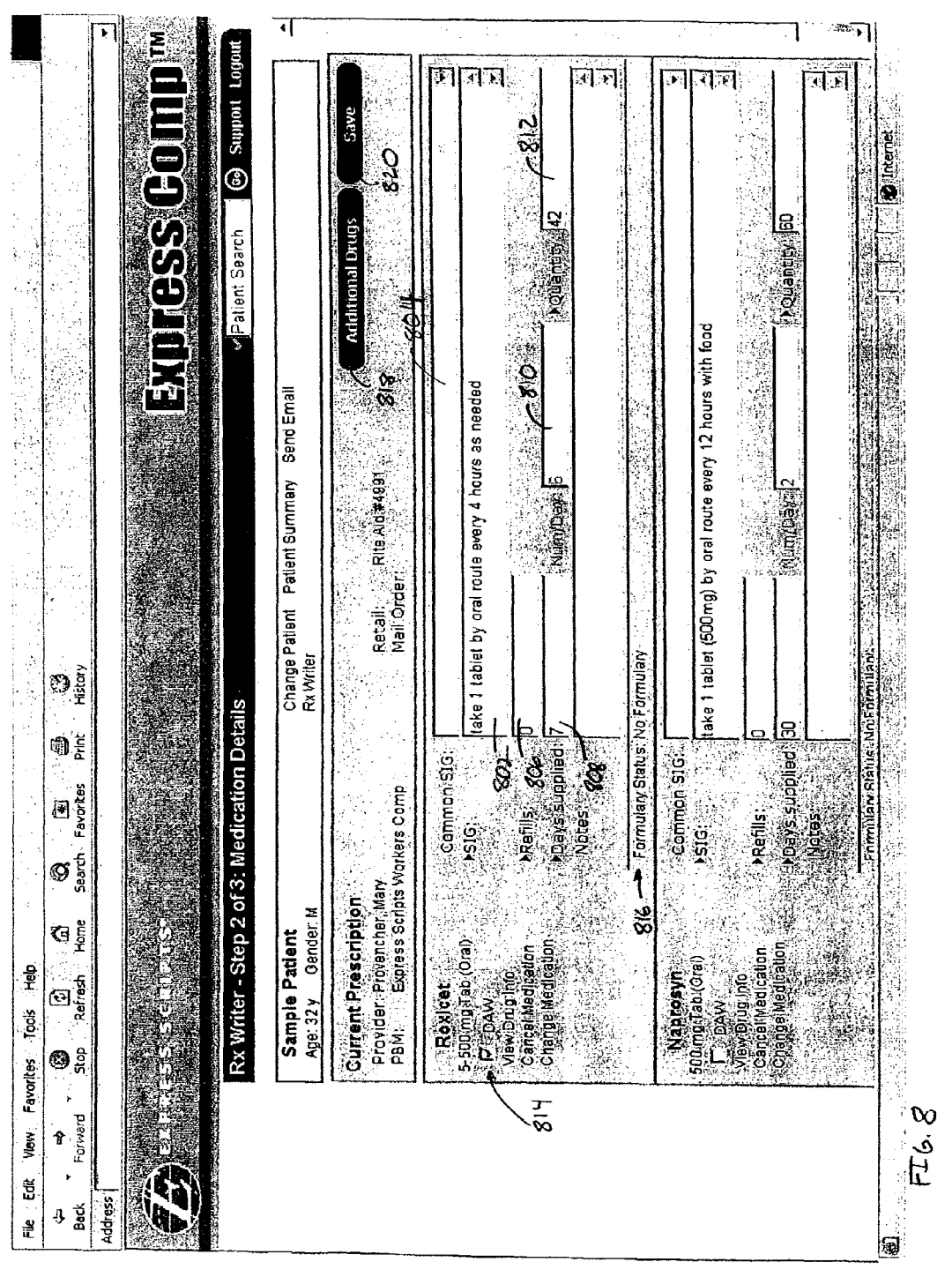

Once the medication has been selected by the user, the program proceeds to step 2 of the prescription writing function: entry of medication details. With reference to FIG. 8, a medication details data entry screen is displayed to the user. The screen allows the user to specify the details regarding each prescription, such as quantity, instructions and refills. Scroll down menu 802 allows the user to select instructions to be printed on the label from a list of common Sigs. This information can be extracted from the drug database. If the user selects a common Sig. appearing in menu 802, the selected Sig. will appear in Sig. text box. The user can modify the selected common Sig. or enter a custom Sig. by typing it into text box 804. In refill text box 806 the user can enter the number of refills. In text box 808, the user can enter the number of days supplied. In the Num/Day text box 810, the user can enter the number of doses to be taken per day. In quantity text box 812 the user can enter the quantity of medications to be dispensed. By selecting DAW box 814, the user can indicate that the medication is only to be dispensed in accordance with the prescription, to prevent the pharmacy from switching to an equivalent medication. Formulary status text line 816, preferably indicates whether prescribed drug is included in the patient's formulary. The user may add additional drugs to the prescription by selecting button 818, which prompts the program to display to the user a medication selection screen (FIG. 7A) to restart the prescription writing process. Once all data has been entered for each prescription, the user may select the save button 820 to proceed to the final confirmation step of the prescription writing process.

Figure 9:
FIG. 9 is an example of a prescription confirmation screen of an embodiment of the method shown in FIGS. 1A-1E.

Once the user has selected the medications to be prescribed and entered the details regarding the prescription, a confirmation screen is displayed as shown in FIG. 9. The confirmation screen can include a patient information box 902 providing information regarding the patient such as the patient's name, age, and gender. A provider information box 904 displays information identifying the provider, PBM and the status of the prescription (e.g., whether the prescription is complete and to be printed or sent electronically to the pharmacy). The user can edit the information displayed in the provider information box 904 by selecting the edit button 905. Prescription information is contained in box 906. Such information can include, for example, an indication as to whether patient wants to have the prescription filled by a retail or mail order pharmacy, information regarding the name and address of the pharmacy, and information regarding each prescription. By selecting patient monograph box 908, the user can prompt the system to retrieve a monograph associated with the drugs prescribed to be printed with the prescription. By selecting the print box 910 the user can prompt the system to print the prescription data and associated information. By selecting the submit box 912 the user can prompt the system to electronically submit the prescription data directly to the retail pharmacy (e.g., via e-mail or facsimile). The user can exit the prescription writing function by selecting exit button 914 or can print or electronically transmit the prescription by selecting go button 916.

Patient Summary

FIG. 10 illustrates an example of a patient summary screen showing various information relating to the patient, which is stored in a patient database. The information can include, for example, demographics information 1002, such as, social security number, date of birth, phone number, e-mail and postal address. Employer information 1004 such as the name of employer, an assigned employer identification number, phone number, and address can be displayed. Medications information 1006 can be displayed, for example, a list of currently prescribed medications. Insurance information 1008 such as the name of the insurance company and policy identification number can be displayed. Workers' compensation claim information 1010 (e.g., injury date, an assigned claim identification number, and actions data indicating treatment provided) can be displayed. If the patient has selected a pharmacy, such pharmacy information 1012 can be displayed. In addition, consent information 1014 indicating whether the employee has given consent to participate in the program, and the date and type of consent given is preferably displayed on the patient summary screen.

Printed Prescription

Figure 11:
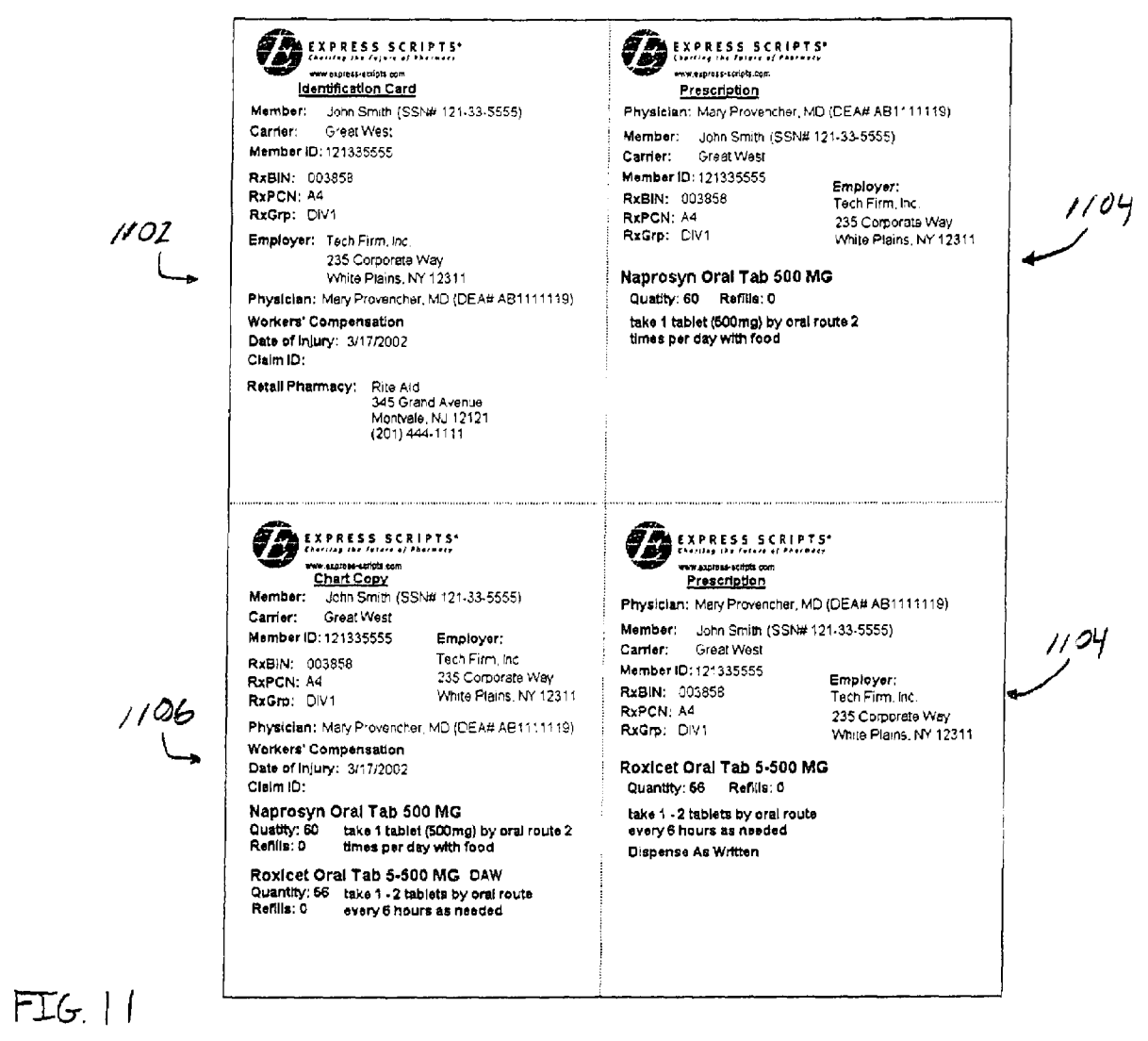

FIG. 11 illustrates an example of an embodiment of a printed document containing prescription data and workers' compensation claim information. The document includes several portions either on separate sheets or, as illustrated in the example shown in FIG. 11, printed on one sheet having multiple segments with perforation between each segment so that they can be easily separated. The segments include an identification card 1102, one or more prescriptions 1104, and a chart copy 1106 for the patient's record.

The identification card 1102 can be presented by the patient to the pharmacy dispensing the prescription. It contains all of the information required for the pharmacy to adjudicate the claim for reimbursement for the cost of the prescription on-line. The identification card preferably includes the member name, the name of the workers' compensation carrier, and a member identification number (which can be the social security number where permitted by law). The identification card also includes routing data to allow the pharmacy to electronically route the workers' compensation claim for on-line adjudication. The routing data preferably complies with NCPDP standards, and includes an identification of the claims processor (RxBIN number), a processor control number (RxPCN) and a group identification (RxGrp number). The BIN number is a routing number used by the switch to identify and route the claim to the processor. The Processor Control Number is used for internal routing by the processor (for example, to designate the claim as a workers' compensation claim). The Group Number can also be used for internal routing by the processor. For example, the Group Number can be used to identify the client (e.g., employer or workers' compensation carrier). The identification card also preferably includes the name and address of the employer, the name of the physician and the physician's DEA number. The identification card can also include information identifying the workers' compensation claim, such as the date of injury and claim identification number. The identification card can also identify the preferred network pharmacy selected by the patient for filling the prescription.

The prescriptions 1104 are also preferably NCPDP compliant and include all information necessary for the pharmacy to fill the prescription and to electronically adjudicate a workers' compensation claim. The printed prescription can include identification and routing data, for example, the physician's name, the patient's name, the patient's social security number, the name of the insurance carrier, the patient's member identification number, the BIN, the Processor Control Number, Group Number, and the name and address of the employer. The prescription also includes an identification of the drug prescribed, quantity, refill information, and instructions. Prescriptions can be printed separately for each separate drug prescribed (as illustrated) or combined on a single document. The chart copy 1106 reflects information contained on the prescriptions and is printed and retained in the patient's record.

Although the invention has been described with reference to a specific embodiment, it will be understood by those skilled in the art that various changes may be made without departing from the spirit or scope of the invention. For instance, the numerous details set forth herein relating to the configuration and operation of the presently preferred embodiment of the web-based software application adapted to facilitate on-line adjudication of prescription drug claims covered by a workers' compensation system are provided to facilitate an understanding of the invention and are not provided to limit the scope of the invention. Accordingly, the disclosure of the embodiment of the invention is intended to be illustrative of the scope of the invention and is not intended to be limiting. It is intended that the scope of the invention will be limited only to the extent required by the appended claims.

We claim:

1. A method comprising:
   receiving, on a computer processor, a point of care identifier;
   verifying, on the computer processor, a point of care location based on receipt of the point of care identifier;
   receiving, on the computer processor, a received patient identifier and a medication identifier associated with a patient from a point of care transmission device, the point of care transmission device associated with the point of care location, the patient receiving medical treatment from a medical professional associated with the point of care location, the patient associated with an employer;
   accessing, on the computer processor, patient data based on the received patient identifier;
   accessing, on the computer processor, eligibility data from a database;
   determining, on the computer processor, that the employer is among a plurality of eligible employers based on the eligibility data to identify the employer as being on-line claim adjudication eligible;
   accessing, on the computer processor, employer data associated with the employer based on identification that the employer is on-line claim adjudication eligible, the employer data including routing data and worker compensation carrier data, the routing data including data to facilitate electronic adjudication of a prescription claim, the worker compensation carrier data including data identifying a worker compensation carrier associated with the employer;

receiving, on the computer processor, injury data associated with the patient, the injury data associated with an injury and an injury date that the injury occurred;

determining, on the computer processor, whether the injury falls within coverage provided by the worker compensation carrier to the employer;

assigning, on the computer processor, a claim identifier to the injury based on a determination that the injury falls within the coverage;

accessing, on the computer processor, medication data associated with medication to treat the injury based on the medication identifier, the medication data including a medication type of a medication and a medication quantity of the medication;

transmitting to the point of care transmission device network display generation data, the point of care transmission device being capable of generating a display of network pharmacies associated with a pharmacy benefit manager (PBM) based on receipt of the network display generation data, the PBM being associated with the employer;

receiving, on the computer processor, a network pharmacy selection based on transmission of network display generation data generation to the point of care transmission device;

generating, on the computer processor, a prescription for the medication, the prescription including the claim identifier, a transmittable patient identifier associated with the patient, the medication type, the medication quantity; and transmitting, on the computer processor, the prescription over an electronic network to a pharmacy device based on receipt of the network pharmacy selection.

2. The method of claim 1, wherein the employer data further includes coverage data and determining whether the injury falls within coverage comprises:

determining, on the computer processor, whether the injury falls within coverage provided by the worker compensation carrier to the employer based on the coverage data.

3. The method of claim 1, further comprising:

receiving a preferred pharmacy selection of a preferred pharmacy from the point of care transmission device;

identifying a plurality of pharmacies located within a prescribed distance from the preferred pharmacy; and generating the network display generation data based on identification of the plurality of pharmacies.

4. The method of claim 1, wherein the point of care identifier is received from the point of care transmission device.

5. The method of claim 1, wherein the transmittable patient identifier is the same identifier as the received patient identifier.

6. The method of claim 1, wherein the received patient identifier includes a patient name of the patient, a date of birth of the patient, a social security number of the patient, a phone number of the patient, or combinations thereof.

7. The method of claim 1, wherein the prescription further includes at least a portion of the employer data.

8. The method of claim 1, wherein the computer processor is deployed within a hand-held computing device at the point of care location.

9. The method of claim 1, wherein the point of care location includes a doctor's office.

10. A non-transitory computer readable medium comprising instructions, which when implemented by one or more processors perform the following operations:

receive a point of care identifier;

verify a point of care location based on receipt of the point of care identifier;

receive a received patient identifier and a medication identifier associated with a patient from a point of care transmission device, the point of care transmission device associated with the point of care location, the patient receiving medical treatment from a medical professional associated with the point of care location, the patient associated with an employer;

access patient data based on the received patient identifier;

access eligibility data from a database;

determine that the employer is among a plurality of eligible employers based on the eligibility data to identify the employer as being on-line claim adjudication eligible;

access employer data associated with the employer based on identification that the employer is on-line claim adjudication eligible, the employer data including routing data and worker compensation carrier data, the routing data including data to facilitate electronic adjudication of a prescription claim, the worker compensation carrier data including data identifying a worker compensation carrier associated with the employer;

receive injury data associated with the patient, the injury data associated with an injury and an injury date that the injury occurred;

determine whether the injury falls within coverage provided by the worker compensation carrier to the employer;

assign a claim identifier to the injury based on a determination that the injury falls within the coverage;

access medication data associated with medication to treat the injury based on the medication identifier, the medication data including a medication type of a medication and a medication quantity of the medication;

transmit to the point of care transmission device network display generation data, the point of care transmission device being capable of generating a display of network pharmacies associated with a pharmacy benefit manager (PBM) based on receipt of the network display generation data, the PBM being associated with the employer;

receive a network pharmacy selection based on transmission of network display generation data generation to the point of care transmission device;

generate a prescription for the medication, the prescription including the claim identifier, a transmittable patient identifier associated with the patient, the medication type, the medication quantity; and transmit the prescription over an electronic network to a pharmacy device based on receipt of the network pharmacy selection.

* * * * *